United States Patent
Miltenyi et al.

(10) Patent No.: US 11,053,470 B2
(45) Date of Patent: Jul. 6, 2021

(54) DISPOSABLE CARTRIDGE FOR ELECTROPORATION

(71) Applicant: Miltenyi Biotec GmbH, Bergisch Gladbach (DE)

(72) Inventors: Stefan Miltenyi, Bergisch Gladbach (DE); Jan Boddenberg, Cologne (DE); Eiad Kabaha, Bonn (DE); Ralf-Peter Peters, Bergisch Gladbach (DE)

(73) Assignee: Miltenyi Biotec, GmbH, Gladbach (DE)

( * ) Notice: Subject to any disclaimer, the term of this patent is extended or adjusted under 35 U.S.C. 154(b) by 285 days.

(21) Appl. No.: 15/252,362

(22) Filed: Aug. 31, 2016

(65) Prior Publication Data
US 2017/0067007 A1   Mar. 9, 2017

Related U.S. Application Data

(60) Provisional application No. 62/215,133, filed on Sep. 7, 2015.

(51) Int. Cl.
| | |
|---|---|
| *C12M 1/00* | (2006.01) |
| *C12M 1/42* | (2006.01) |
| *C12N 15/87* | (2006.01) |
| *A61N 1/32* | (2006.01) |
| *C12N 13/00* | (2006.01) |

(52) U.S. Cl.
CPC ............. *C12M 35/02* (2013.01); *A61N 1/327* (2013.01); *C12M 23/28* (2013.01); *C12N 13/00* (2013.01); *C12N 15/87* (2013.01)

(58) Field of Classification Search
CPC ....... C12M 35/02; C12M 23/28; A61N 1/327; C12N 15/87; C12N 13/00
USPC .......................................... 435/285.2, 289.1
See application file for complete search history.

(56) References Cited

U.S. PATENT DOCUMENTS

6,653,136 B1 * 11/2003 Dodgson ................ C12M 35/02
435/285.2
6,942,771 B1 * 9/2005 Kayyem ................ B01L 3/5027
204/409

(Continued)

OTHER PUBLICATIONS

David Selmeczi et al, "Efficient large volume electroporation of dendritic cells through micrometer scale manipulation of flow in a disposable polymer chip", Biomedical Microde Vices, Kluwer Academic Publishers, vo 13, No. 2 Jan. 5, 2011, pp. 383-392.

(Continued)

*Primary Examiner* — Liban M Hassan
(74) *Attorney, Agent, or Firm* — Jaquelin K. Spong

(57) ABSTRACT

The invention is directed to disposable cartridge for electroporation of cells, comprising a fluid compartment in an interior of the disposable cartridge; a first fluid port for providing cell suspension to the fluid compartment, and a second fluid port for delivering a fluid comprising at least one compound to be electroporated into the cells to the fluid compartment; a first electrode and a second electrode disposed in the fluid compartment; at least one exit port which delivers the fluid from the fluid compartment wherein the first and second fluid port have a fluid communication to a mixing channel which has a fluid communication to the fluid compartment, and a third ground electrode and a fourth ground electrode.

18 Claims, 11 Drawing Sheets

(56) References Cited

U.S. PATENT DOCUMENTS

| | | | | |
|---|---|---|---|---|
| 7,771,984 | B2* | 8/2010 | Dzekunov | C12M 41/00 204/643 |
| 2004/0058423 | A1* | 3/2004 | Albritton | G01N 27/44743 435/173.7 |
| 2004/0141880 | A1* | 7/2004 | Handler | B01L 3/502715 506/15 |
| 2007/0105206 | A1* | 5/2007 | Lu | C12M 35/02 435/173.6 |
| 2007/0190525 | A1* | 8/2007 | Gu | B01L 3/502715 435/5 |
| 2010/0068706 | A1* | 3/2010 | Pourahmadi | B01L 7/52 435/6.19 |
| 2011/0275111 | A1* | 11/2011 | Pettigrew | B01L 3/502776 435/29 |
| 2012/0190040 | A1* | 7/2012 | Talebpour | B01L 3/502753 435/7.1 |
| 2013/0089930 | A1* | 4/2013 | Joo | C12M 23/16 435/450 |
| 2013/0295588 | A1* | 11/2013 | Watkins | C12M 41/36 435/7.24 |
| 2014/0170646 | A1* | 6/2014 | Kelley | C12N 1/066 435/6.11 |

OTHER PUBLICATIONS

Geng T et al "Flow-through electroporation based on constant voltage for large-volume transfection of cells" Journal of Controlled Release, Elsevier, Amsterdam, NL, vol. 144. No. 1, May 21, 2010 pp. 91-100.

Fox M B et al "Electroporation of cells in microfluidic devices: a review" Analytical and Bioanalyticl Chemistry, Springer, Berlin, DE vol. 385, No. 3, Mar. 14, 2006, pp. 474-485.

* cited by examiner

Fig. 3 Top view

Fig. 5b Lower Inner surface

Fig. 5a Lower Outer surface

Fig. 6a Lower surface of assy

Fig. 6b Upper surface of assy f) microfluidic mixed sample e) sequentielly filled sample without microfluidic mixing

DISPOSABLE CARTRIDGE FOR ELECTROPORATION

CROSS REFERENCE TO RELATED APPLICATIONS

This US Patent Application is a non-Provisional application claiming priority to U.S. Provisional Patent Application Ser. No. 62/215,133, filed Sep. 7, 2015 and hereby incorporated by reference.

STATEMENT REGARDING FEDERALLY SPONSORED RESEARCH

Not applicable.

STATEMENT REGARDING MICROFICHE APPENDIX

Not applicable.

BACKGROUND

This invention relates to performing electroporation of cells.

Electroporation, or electropermeabilization, is a molecular biology technique in which an electrical field is applied to cells in order to increase the permeability of the cell membrane, allowing nucleic acids to be introduced into the cell.

Electroporation is used to introduce nucleic acids into cells, especially mammalian cells. The transferred nucleic acids can be used for transient protein expression. Especially mRNA electroporation is used to transiently express proteins of interest. Plasmid can be used for transient expression as well as for stable integration. The integration of plasmid into the genome can be improved by introducing double strand breaks and homologous sequences that will replace the broken genome segment by homologous recombination. Another possibility is to use transposases to integrate genetic information flanked by transposase motivs into the genome. Transferred nucleic acids can also encode for nuclease. Site specific nucleases are a common tool to knock out genes by non-homologous end joining.

Thereby, electroporation can be used in the process of producing knockout or transgenic cells. Using animal embryonic cells, transgene or knockout cells can also be used to develop transgenic or knockout animals. Cells modified by nucleic acid electroporation, are used for tumor treatment, gene therapy, or other cell-based therapies.

Electroporation is performed with electroporators, purpose-built appliances which create an electrical field applied to a cell suspension containing the nucleic acids to be transferred into the cells. Usually, the cell suspension is pipetted into a glass or plastic cuvette which has two electrodes on its sides. Prior to electroporation, the cell suspension is mixed with the nucleic acids to be transformed. The mixture is pipetted into the cuvette, the voltage and capacitance are set, and the cuvette is inserted into the electroporator. The electroporator will apply an electrical field. The electric field is defined by the field strength, e.g. the applied voltage per distance of the electrodes, the time and the capacitance. For exponential decay pulses, the voltage and capacitance are set and the electric field decays due to the current passing the cell suspension. For square wave pulses, a high capacitance is used and an electric field is applied for a given time. Due to the high capacitance, the decay of the electric field by the current passing the cell suspension should be minimal. During the electroporation, the electric fields generates holes in the cell membrane allowing also larger molecules like nucleic acids to pass the cell membrane. Bilayer lipid membranes, like cell membranes, can be disturbed by an intense transmembrane electric potential as disclosed by Tsong, T. Y., "Electroporation of cell membranes", Biophys J, 1991. 60(2): p. 297-306. If a transmembrane electric field exceeds the dielectric strength of a cell membrane, the membrane conductance increases dramatically. This breakdown potential has been reported by Tsong et al. between 150 and 500 mV for μs to ms field durations for lipid bilayers of 5 nm thickness. This translates into dielectric strength of 300-1000 V/cm. Penetration of low molecular weight molecules has been detected for electric field strength >0.3-0.4 kV/cm by Rols, M. P. and J. Teissie, "Electropermeabilization of mammalian cells to macromolecules: control by pulse duration". Biophys J, 1998. 75(3): p. 1415-23. The threshold field intensity for membrane permeabilization has been described by Wolf, H., et al., "Control by pulse parameters of electric field-mediated gene transfer in mammalian cells", Biophys J, 1994. 66(2 Pt 1): p. 524-31 to be 580 V/cm.

The electrical potential difference a cell membrane encounters has been described by:

So, the potential difference is proportional to the initial electric field strength E0 and the radius r of the cell (Neumann, E., et al., Gene transfer into mouse lyoma cells by electroporation in high electric fields. Embo J, 1982. 1(7): p. 841-5).

For a typical cell radius of 5 μm, the permeablization threshold of e.g. 300 mV can be achieved by an electric field strength >400 V/cm. For a smaller cell (r=1 μm), the required field strength can be estimated to at least 2000 V/cm.

Besides passive diffusion of the nucleic acids into the cells, additional electrophoresis of the nucleic acids in an electric field can be applied. The electric fields needed for electrophoresis are smaller than for the electroporation. Exponential decay pulses likely permeablize the cell membrane with the high electric field at the beginning and the decaying field subsequently transports the nucleic acids into the cells. For square wave pulses, two or more pulses can be generated to combine electroporation and electrophoresis.

Nucleic acids can be DNA or RNA. As DNA is more stable, mixing the DNA e.g. plasmids together with the cell suspensions usually doesn't harm the DNA. In contrast, RNA is prone to degradation e.g. by RNases secreted by cells or from contaminated buffers. Therefore, RNA is usually added before the electroporation step to minimize the risk of RNA degradation before the RNA can enter the cell. Within the cell, the RNA becomes protected by nucleic acid binding proteins and the translation machinery.

For an automated electroporation device, nucleic acids, especially RNA should also be mixed with the cell suspension just before the electroporation. Currently, mixing of nucleic acids and cell suspension followed by an electroporation step cannot be performed automatically. Whereas there are many devices for semi-automated or automated electroporation, the sample preparation e.g. mixing of nucleic acids and cell suspension has to be performed beforehand the electroporation process. The mixing process comprises adding the two solutions, e.g. cell suspension and nucleic acid solution, at a constant ratio to produce a homogenous mixture.

The concentration of nucleic acids during the electroporation process is crucial and for reproducible results, the defined ratio needs to be maintained during the process. The same is true for the homogeneity of the mixture. For homogenous cell electroporation, the local nucleic acid concentration should be the same for all cells. In homogenous mixing will give rise to a mixture of cells with no nucleic acids, low amounts and high amounts. As the electroporated cells will usually be cultivated after electroporation or even given to patients, the mixing and electroporation process has to be performed in a sterile environment.

Accordingly, there is a need in the art for a device allowing mixing of nucleic acids and cells and enabling electroporation of the cells under sterile conditions.

SUMMARY

The present invention is directed to a disposable for electroporation of cells, comprising
- a fluid compartment in an interior of the disposable;
- a first fluid port for providing cell suspension to the fluid compartment, and a second fluid port for delivering a fluid comprising at least one compound to be electroporated into the cells to the fluid compartment;
- a first electrode and a second electrode disposed in the fluid compartment;
- at least one exit port which delivers the fluid from the fluid compartment wherein the first and second fluid port have a fluid communication to a mixing channel which has a fluid communication to the fluid compartment.

The disposable cartridge allows mixing of at least two fluids at a given ratio to achieve a homogenous, combined fluid. This mixing is accomplished by a microfluidic device defining the volumetric mixing ratio and enabling homogenous fluid mixing. The cartridge can be mounted in a tubing set allowing sterile cell handling. A peristaltic pump or a vacuum pump is used to move fluids into and out of the electroporation assembly thereby minimizing the risk of leakage or defects. The tubing set can also be combined with other cell processing steps like cell separation or cell cultivation.

BRIEF DESCRIPTION OF THE DRAWINGS

Various exemplary details are described with reference to the following figures, wherein.

DETAILED DESCRIPTION

Figure 1:
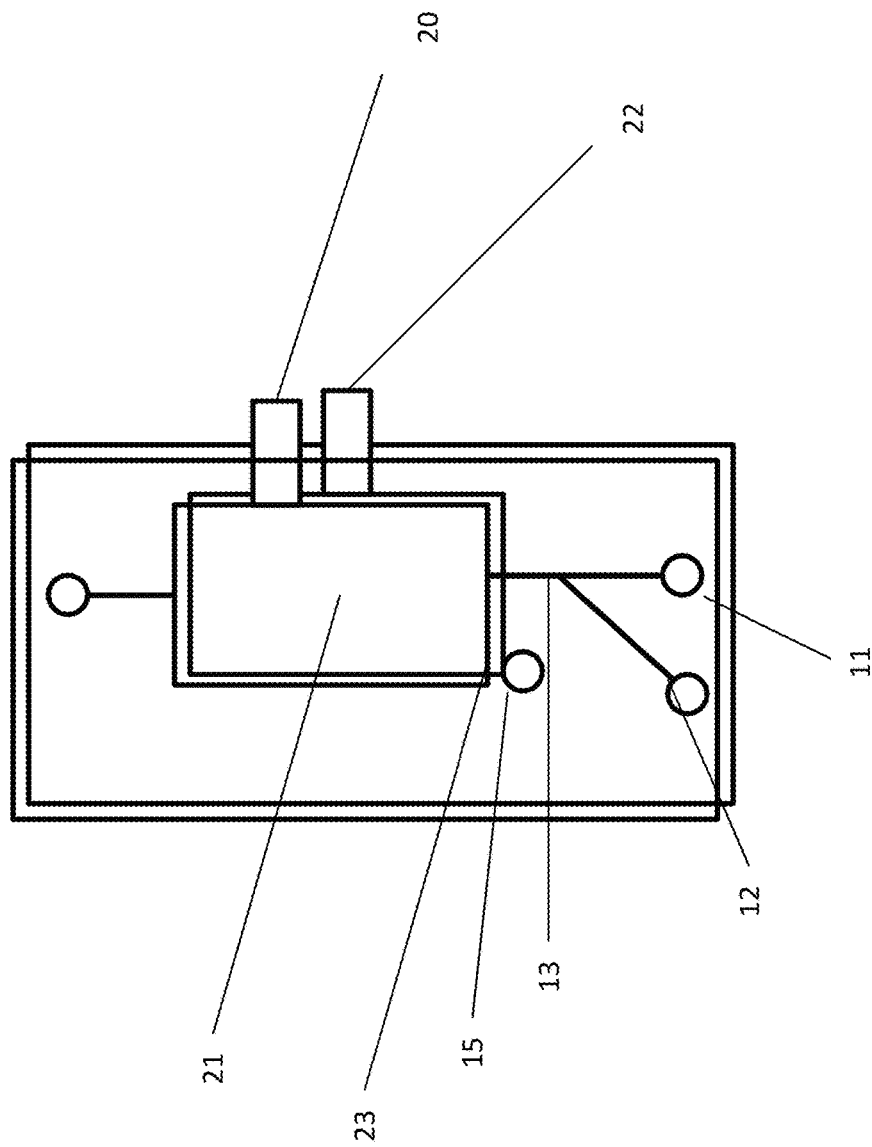
FIG. 1 is a perspective view of a generic embodiment of a disposable electroporation cartridge assembly.

The device of the invention enables the transfection of cells by the mixing of at least two fluids comprising cells and at least one compound to be electroporated into the cells with a predefined volumetric mixing ratio and applying an electric field to the mixed fluids.

The compound to be electroporated into the cells can be any compound known in the art to be useful for electroporation, like nucleic acids, oligo nucleotides, poly nucleotides, DNA, RNA, peptides, proteins and small molecules like hormones, cytokines, chemokines, drugs, or drug precursors. In the following, the term "nucleic acids" as compound to be electroporated is used as synonym for all such compounds to be electroporated, like oligo nucleotides, poly nucleotides, DNA, RNA, peptides, proteins and small molecules like hormones, cytokines, chemokines, drugs, or drug precursors.

In order to perform electroporation on a homogeneously mixed fluid and to prevent laminar flow in the channels, the mixing channel of the disposable has a serpentine shape and/or comprises agitator elements and/or a mixing chamber. After mixing the cell suspension and the nucleic acid solution, an electric field is applied, which induces pores in the cell membranes. Nucleic acids can then enter the cells through the pores either by diffusion or electrophoresis.

In one embodiment of the device, the volumetric mixing ratio of the at least two fluids is defined by at least two microfluidic channels having different microfluidic resistance, i.e. the first fluid port and the second fluid port fluid port are provided with channels having different microfluidic resistance to the fluids.

The flow of each fluids depends on the resistance of the respective channel, for example channel 112 and 122 in FIG. 4a. Less fluid will pass the channel with higher resistance as compared to the at least other channel having a lower resistance. Thereby, the mixing ratio can be defined by the ratio of resistances of the at least two input channels. Preferable, the first fluid port and the second fluid port fluid port are provided with channels having a microfluidic resistance to maintain a mixing ratio of 1:5 to 1:10 of the first fluid to the second fluid. Using different volumes results in changes in the hydrostatic pressure of each solution. Thereby, the hydrostatic pressure differences impaired the mixing ratio defined by the microfluidic channel resistances.

The fluids may be pumped or sucked into the device. Accordingly, the first fluid port and the second fluid port fluid port of the disposable are in fluid communication to at least one pump delivering fluids into the fluid compartment and/or at least one exit port is in fluid communication to at least one vacuum source thereby sucking fluids into the fluid compartment.

The pump or vacuum source should provide a pressure difference of at least 100 mbar between the first fluid port and the second fluid port on one side and the at least one exit port is in fluid on the other side. Preferable, the pressure difference is between 100 and 800 mbar, especially between 200 and 500 mbar.

The mixed fluids are forced by the pressure difference into the fluid compartment between the two electrode plates of the device. The filling process i.e. the filling level of the fluid compartment can be controlled and/or automatized by measuring the capacitance between the first and second electrode. Filling may continue until, for example, the maximum capacity between the first and second electrode is reached. In alternative, the electrical resistance between the grounding electrodes (as explained later) can be used to determine the filling level of the fluid compartment. In alternative, the filling level may be determined by controlling the pressure difference applied to the fluid compartment. By controlling the filling level of the fluid compartment, the device can be operated in a semi-continuous mode.

After filling the volume between the electrode plates, an electric field is applied. The electric field is usually given as electric pulse. The shape of the pulse can be exponential decay, square wave or different combinations. Importantly, the electric field strength must be sufficient to create pores in the cell membranes. The nucleic acids can then enter the cells either by diffusion or electrophoresis. The electroporated cells are then cleared from the device, optionally for further processing like, detecting, enriching and/or depletion of certain subsets of cells and/or cell culturing. To electroporate more cells (higher amounts of cells or higher volume of cell suspension), the process of filling, mixing, electroporation and clearance can be repeated. In addition, the electroporation process itself can be repeated on the same cell sample, with or without washing, culturing or separation step.

The applied electric field can destroy electrodes made from of metals like aluminum. To allow multiple electroporation sequences of the device using the same electrode plates, the plates can be coated with metals resistant against electrochemical corrosion. Conductive coatings like noble metals e.g. gold can be used to protect the electrode plates. In a variant, the disposable of the invention comprises a first metal electrode and the second metal electrode made from titanium covered with a layer of gold. To avoid different field intensities between the electrodes, the electrodes should by arranged in parallel with a constant distance to each other over the whole surface of the electrodes. Preferable, the first metal electrode and the second metal electrode are separated by a distance of 2-4 mm in a parallel arrangement with variations in distance less than +−20 μm. Furthermore, the surface of the electrodes should be as smooth as possible without pin holes or peaks. Electrodes having a roughness Rz of 1 to 10 μm are preferred.

FIG. 1 is a perspective view of a simplified disposable electroporation cartridge. Elements in the cartridge are an input port 11 a second input port 12, and they mixing column 13. On the input port 11, second input port 12, and mixing column 13 comprise the input elements to the disposable cartridge 10. Upon exiting the mixing column 13, the sample fluid then enters a cavity which includes first electrode 21 and second electrode 23. Electrodes 21 and 23 maybe parallel plane capacitors, such that elements 21 and 23 are flat plane or conductive structures separated by a small gap. Voltage is applied to plate 21 and 23 by tabs 20 and 22 and the fluid exits the disposable cartridge through exit port 15.

A fluid sample maybe introduced through input port 11, additive elements such as, for example RNA, enters through secondary input port 12. For example, a cell suspension may be introduced through input port 11 and a nucleic acid solution is filled via the second input port 12. The cell suspension and the nucleic acid solution are mixed in mixing channel 13 and introduced into a cavity which contains the electrostatic plates of 21 and 23.

The cell suspension, having been mixed with the nucleic acid solution, flows through the gap between plates 21 and 23 and is subjected to the electric field applied between the two plates. As is well-known in the art, this electric field generates pores in the cell membranes, allowing the nucleic acid to diffuse into the cell. After the electroporation, the amended cells then can be removed from the disposable by the exit port 15.

Figure 2:
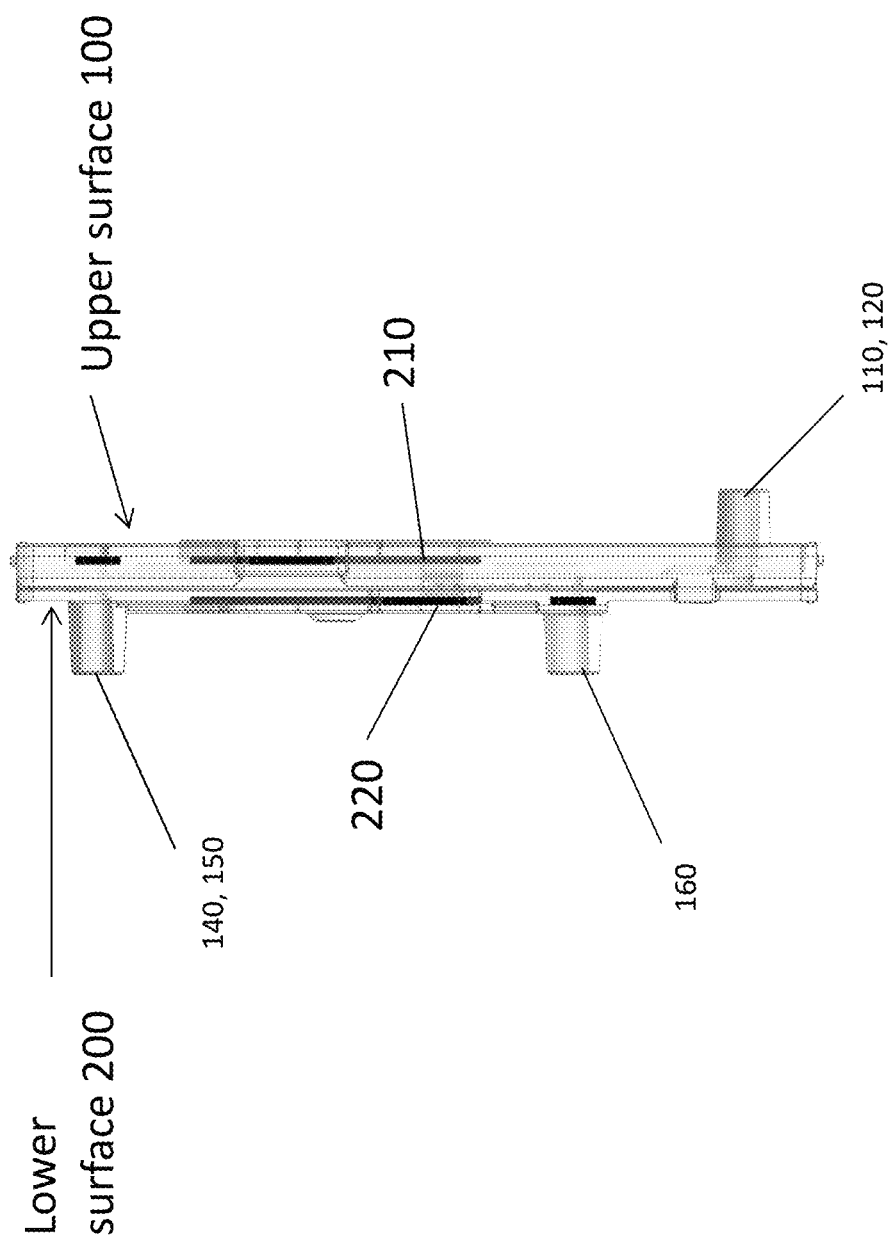
FIG. 2 is a side view of the disposable electroporation cartridge assembly.

The disposable according to invention is preferable formed by joining two halves of the disposable, the halves comprising respectively the first or the second electrode. This embodiment is shown in more detail in FIG. 2 in side view. Disposable electroporation cartridge 10 maybe composed of two parts, an upper surface 100 and a lower part 200. These two parts may be made of molded plastic, and weld together by laser radiation or a HF field. The disposable, electroporation cartridge 10, may further include an additional port 160 and two exit port 140, and 150, the function of which will be described below. Finally, the disposable electroporation cartridge 100 may also include the two electrode plates 210 and 220, which are separated by a gap. The distance between the two electrodes (gap) will be chosen according to the applied voltage and the required electric field. Common electrode distances are 2 to 4 mm. Smaller gaps might be favorable for to enable high electric fields of more than 2 kV/cm, for example, 100 μm. In addition, the gap has to be sufficient to allow the flow of the inlet fluid and should not harm the cells e.g. by shear stress. In some embodiments, the electric field maybe in the order of 2 kV/cm.

Figure 3:
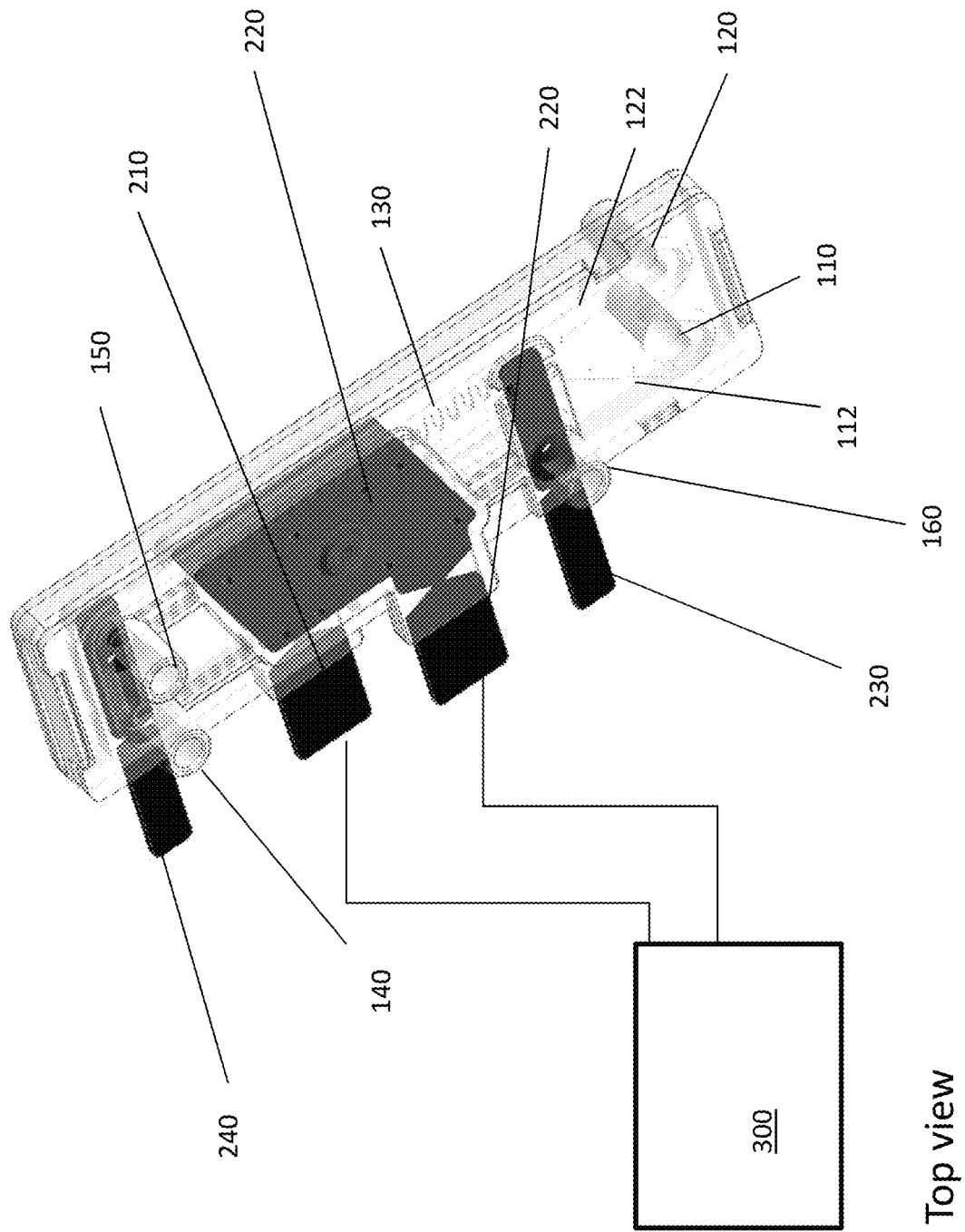
FIG. 3 is a perspective view from above of a disposable electroporation cartridge assembly.

FIG. 3 is a perspective view of an assembled disposable electroporation cartridge 10. The assembled view includes the upper surface 100 and the lower surface 200 which are shown together and FIG. 3 also shows the two input ports 110 and 120 in this lower surface 100, along with the first electrode plate 210 also in the lower surface 100.

In the upper surface 200 are the two exit ports 140 and 150, along with the second electrode plate 220. It should be understood that the terms of upper and lower, are arbitrary, and the cartridge 10 may be viewed in any arbitrary orientation. FIG. 3 also shows the output ports 140 and 150, which are on the upper surface 200. Lastly, the upper surface 200 may also include, as can be seen in FIG. 3, the mixing channel 130 connected to the first input channel 110, and the secondary input channel 120. The mixing channel is intended to mix the contents of the two input channels. Mixing channel 130 maybe of the serpentine shape or any other structure supporting the two fluids to merge. The mixing cannel 130 introduces the mixed fluid into the cavity containing the electrode plates 210 and 220. The mixing channel 130 may include between five and 15 serpentine turns. The serpentine turns causes the chaotic mixing of the two components, the cell suspension and the nucleic acid solution.

The fluid compartment is preferable shaped as to enable bubble-free filling and draining. Therefore, the mixing channel and at least one exit port may be located at the most opposite sides of the fluid compartment i.e. at the highest and lowest point of the fluid compartment. In addition, the fluid compartment and the electrode plates 220 and 230 may have a particular shape which avoids dead space, like obtuse angles and/or acute angle. As illustrated in FIG. 3, the fluid compartment and optional the plates may have a parallelogram, or trapezoidal shape.

It should be understood that this parallelogram is an exemplary embodiment, and that the shape of the fluid compartment and the electrodes maybe any arbitrary shape, including rectangular, circular, trapezoidal, or any other shape according to the requirements of bubble-free filing of the device.

Figure 4:
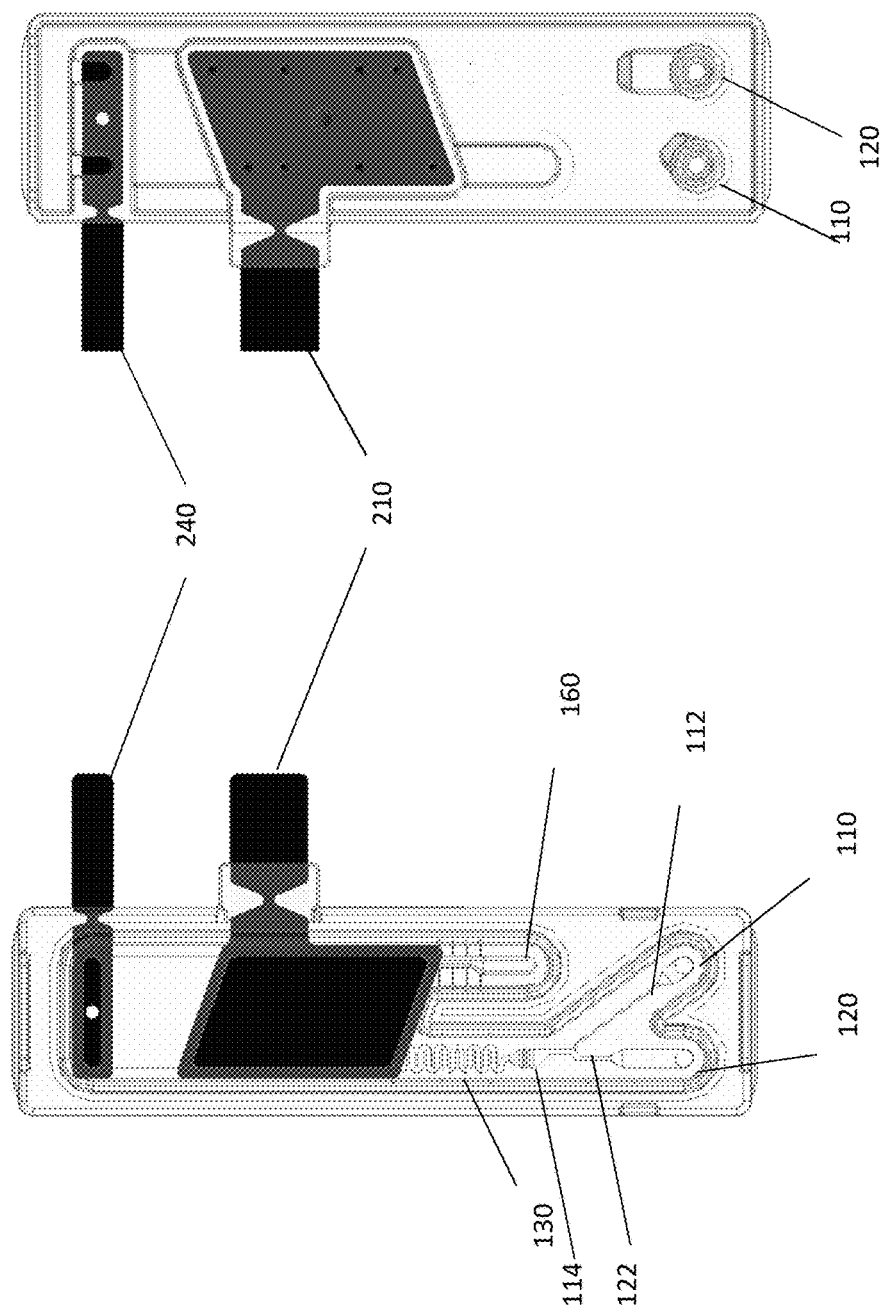
FIG. 4a is a plan view of the outer surface of the lower half of the disposable electroporation cartridge assembly of FIG. 3.
FIG. 4b is a plan view of the inner surface of the lower half of the disposable electroporation cartridge assembly of FIG. 1.
Figure 5:
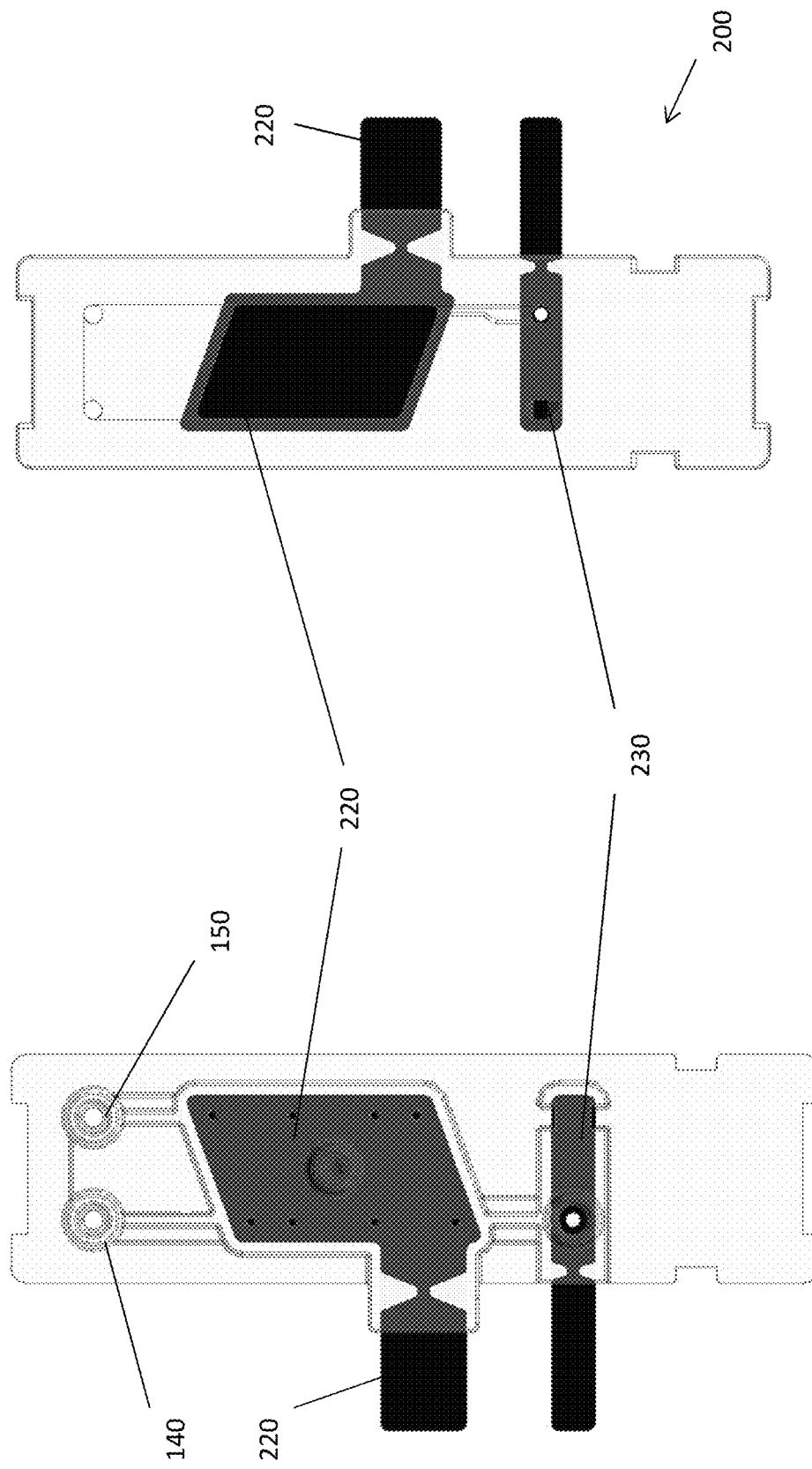
FIG. 5a is a plan view of the outer surface of the upper half of the disposable electroporation cartridge assembly of FIG. 3.
FIG. 5b is a plan view of the inner surface of the upper half of the disposable electroporation cartridge assembly of FIG. 3.

In another embodiment of the invention, the disposable comprises further at least one additional electrode which applies a ground potential to at least one of the first fluid port, second fluid port or exit port. This embodiment is shown in FIGS. 3-5 with grounding tabs 230 and 240. These tabs may be used to apply a ground potential to the entering fluid in channel 112 and 122 and to the exit channels 140 and 150 accordingly. The fluid input and exiting from the cavity that contains electrode plates maybe at ground potential.

FIGS. 4A and 4B illustrate in greater detail some of the features of the upper surface 100, which was shown in FIG. 3. FIG. 4A shows the outer surface of upper piece 100, and FIG. 4B shows the inner surface of the upper portion 100. As shown in FIG. 4A, the upper portion 100 may include the two input ports 110 and 120, along with the electrode plate 210. Finally, the upper portion may also include grounding tab 240.

FIG. 4B has topography that is associate with those structures. For example, the inner surface of upper structure 100 may have a channel 112 that is associated with input port 110. This channel 112 may serve to deliver the fluid from the input port 110 to the mixing channel 130. Similarly, the inner surface of the upper portion 100 may also have another channel 122 associated with the secondary input port 120. Channel 122 serves to deliver the additional material that is introduced through second port 120 to the mixing channel 130. The diameter and length of the channel 112 and 122 define a microfluidic resistance. The proportion of the microfluidic resistance is used to define the ratio of the two fluids delivered through input port 110 and 120 respectively. In the depicted assembly, channel 112 comprises a longer narrow part as compared to channel 110 for which the narrow part is shorter.

The mixing channel 130 as previously described, may have a serpentine shape which serves to mix the contents of channel 122 with the contents of channel 112. In this variant of the disposable, the contents of channel 122 with the contents of channel 112 is further enhanced by mixing chamber 114. Mixing chamber 114 provides a volume where a possible laminar flow of the fluids is converted into turbulent flow.

In one exemplary embodiment, secondary input channel 110 serves to deliver nucleic acid to a cell suspension that is input to input channel 112. The nucleic acid solution is mixed with the target cells that are included in the input fluid which was introduced to input port 120. At the mixing channel 130 the nucleic acid is mixed with the target cells such that the fluid entering the cavity has those combined elements.

The footprint of the electrode plate to 210 is also shown in FIG. 4B. In this view, the lower corner of electrode plate 210 can be shown to be coupled to the output port 160.

Also shown in FIG. 4B is the metallic tab 240. This tab may be used to apply a ground potential to the exit ports 140 and 150 accordingly. The fluid exiting from the cavity that contains electrode plates maybe at ground potential.

FIGS. 5A and 5B show the inner and outer surfaces of the lower portion 200 Like FIGS. 4A and 4B, included in the illustration are the electrodes and the output and the ports. And particular the lower portion 200 may include an electrode 220 and its associated metallic tab 220, along metallic tab 230. As described previously, electrode plate 220 may serve to be the opposite plate of a parallel plate capacitor, which is formed by electrode plate to 210 and electrode plate 220.

Lastly, the lower surface 200 may also contain the exit ports 140 and 150. As shown in FIG. 5A, the exit port 150 maybe couple to the rising shoulder of the cavity, whereas exit port 140 maybe couple to the lower shoulder of the cavity. In this way, exit 150 may serve to evacuate air e.g. bubbles from the cavity.

Figure 6:
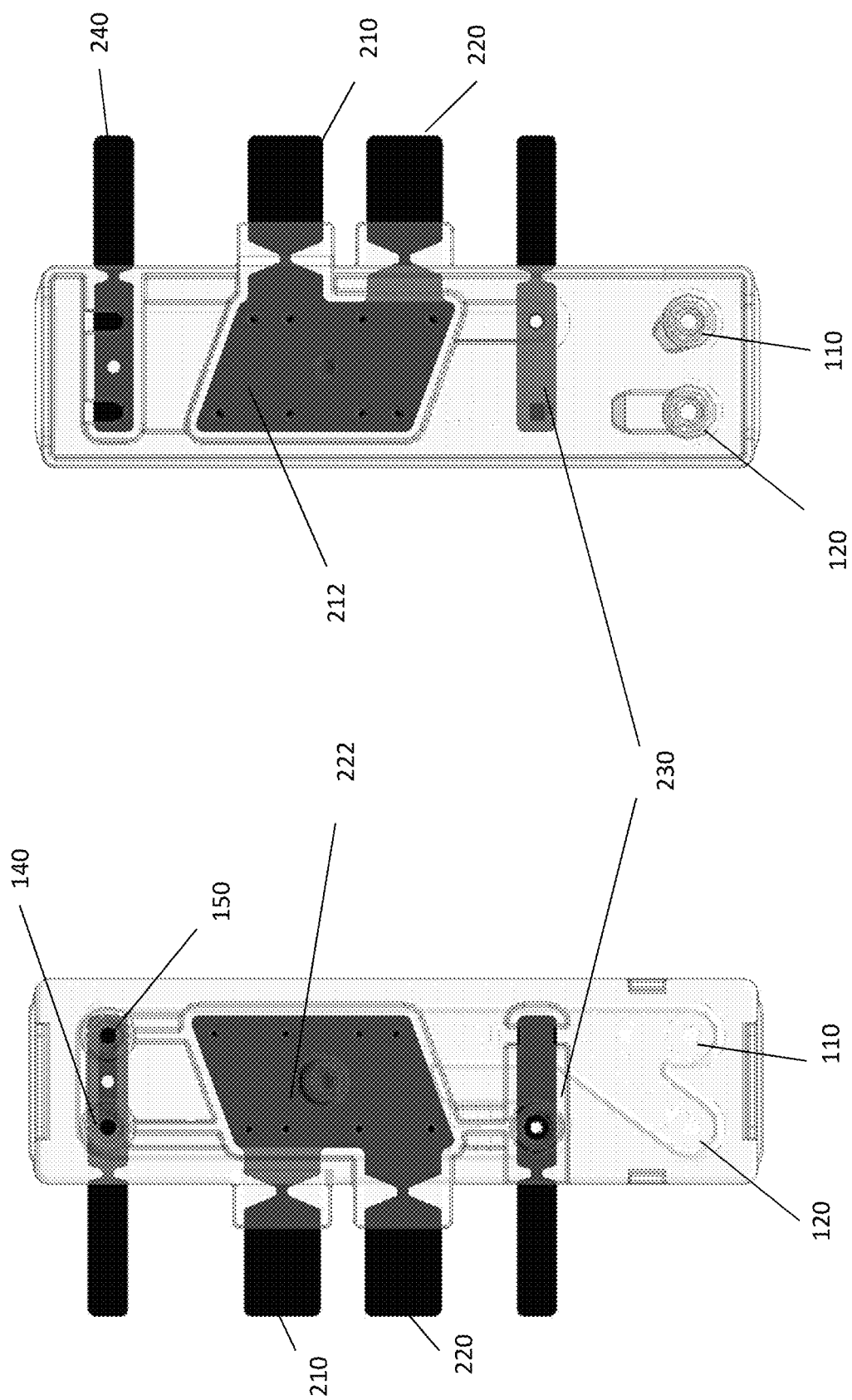
FIG. 6a is a plan view of the lower surface of the disposable electroporation cartridge assembly of FIG. 1.
FIG. 6b is a plan view of the upper surface of the disposable electroporation cartridge assembly of FIG. 1.
Figure 7:
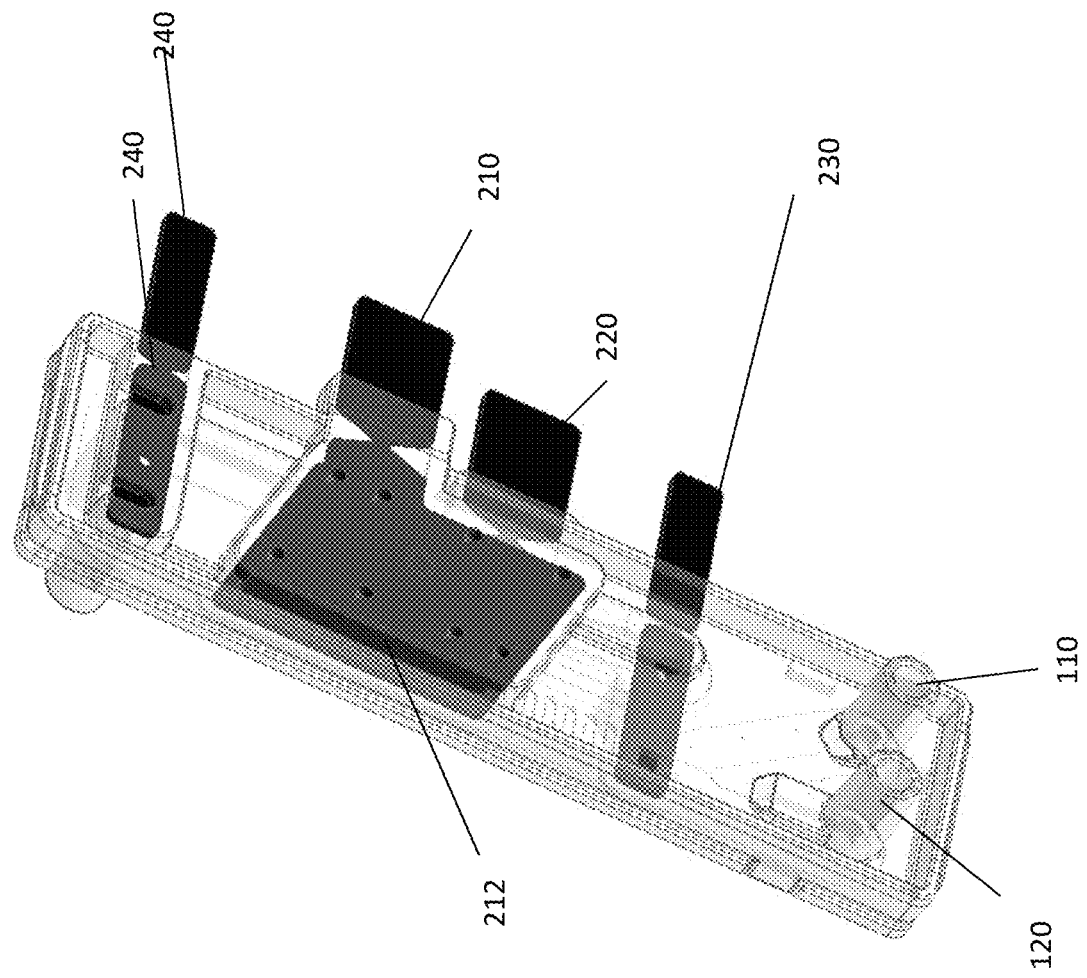
FIG. 7 is a perspective view of the lower surface of the disposable electroporation cartridge assembly of FIG. 3.

FIGS. 6A and 6B are plan views of the completed cartridge assembly. FIG. 6A shows from below, whereas FIG. 6B shows a view from above. Once again, it should be understood that the terms "below" and "above" are arbitrary, and the cartridge may be held in for ease of clarity, however, FIG. 6A is referred to as a few from below, and FIG. 6B is referred to as a view from above. In either case, the cartridges are shown as assembled, with the upper portion 100 joint to the lower portion 200. Included in the assembly are, once again, the two input ports 110 and 120 and the exit ports 140, 150, and 160. Also shown are the grounding taps 230 and 240, as well as the electrode plates 220 and 210.

As was described briefly above, the disposable cartridge assembly 10 may be constructed from injection molded plastic like polystyrene, poly ethylene, poly propylene or poly carbonate. Outlines of the various structures, including the electrostatic plates 210 and 220 may be formed in the plastic material. In addition, locating areas for the grounding tabs. As with FIG. 6, the two input ports 110 and 120 are shown as affixed to the upper portion 100, and the exit towards 140 and 150 or shown as couple to the lower portion 200. In addition, grounding tabs 230 and 240 our best shown from below. The fluid orifices 110, 120, 140, 150, and 160 may be formed in the injection molded plastic material. At the same time, the serpentine structure and/or the agitator elements of the mixing channel and the optional mixing chamber may also be formed in the appropriate part of the disposable. Locating areas for all the metallic components, including the grounding straps 230 and 240, and electrode plates 220 and 210 maybe formed in the appropriate elements. The injection molded plastic may be found with the seating area for each of these components. The metal parts can be directly molded into the parts. Alternatively, glue may be applied to the plastic material and the metal structures may be glued in place. Once the electrode plate 220 is formed in the lower portion 200, and electrode plate 210 is formed in the upper portion 100, the upper and lower portions maybe assembled together. The assembly may be fixed by laser welding, HF welding, plasma bonding, gluing or any other technique suitable to fix two plastic parts together may be used.

After fabrication, further fluid elements like tubings maybe joined to the two input ports 110 and 120, as well as the exit ports 140, 150, and 160. A pneumatic source maybe coupled to the exhaust port 160. The pneumatic element may serve to suck liquids into the gap between the electrodes.

The voltage supply 300 maybe coupled to the metallic tabs 210 and 220, in order to apply a voltage potential between the two electrode plates 210 and 220. Vacuum is then applied to the exit port 140 or 150 and thereby also to channel 130 and input port 110, as well as the secondary input port 120. The fluid extremes are mixed in the mixing channel 130, and the fluid is allowed to pass through the cavity, and between the electrodes 210 and 220. After the space between the electrodes has been filled, an electric field can be applied. The electric field induces pores into the cell membranes, allowing the nucleic acids enter the target cells by diffusion or electrophoresis. Upon exiting through the exit port 160, the fluid stream includes target cells loaded with the nucleic acids. The total time for this to take place will depend on the application, but maybe on the order of 10 to 20 minutes. The total cavity volume may be on the order of 0.05 to 5 ml.

Another object of the invention is a process for electroporation of cells in the disposable as already disclosed, wherein a cell suspension is provided to a first fluid port as first fluid and a fluid comprising at least one compound to be electroporated into the cells is provided to the second fluid port as second fluid; the first and second fluids are provided to the fluid compartment in predefined mixing ratio by applying a pressure difference between the first and second fluid port and at least one exit port; applying an electric field between the first and second electrode thereby electroporating the cells with at least one compound; and removing the fluids from the fluid compartment.

The process of the invention may be conducted in several variants. To enable automatic continuous or semi-continuous processing, the first and second fluids are provided to the fluid compartment to a predefined filling level. The filling level of the fluid compartment may be determined by measuring the capacitance between the first and second electrode, for example measuring the capacitance until the maximum capacity is reached. In another variant, the filling level is determined by measuring the resistance between the grounding electrodes (230 and 240 in FIG. 3). Furthermore, the filling level might be controlled via the pressure difference applied to the disposable.

In another variant of the process, after removing the fluids from the fluid compartment, the electroporated cells are detected and depleted from the fluids. The thus concentrated electroporated cells might be further processed and/or cultivated. The detection of the electroporated cells and their depletion may be accomplished by methods known to a person skilled in the art for cell sorting like FACS or magnetic sorting. On the other hand, the not electroporated cells (depleted from the electroporated cells) can be provided to another electroporation process step to enhance the overall yield of electroporation.

In yet another variant of the process, the electroporated cells are cultivated after removing the fluids from the fluid compartment. Any method known to a person skilled in the art can be used for cultivation. In a preferred embodiments, cultivation is performed in a centrifuge chamber as for example disclosed in WO2009072003A2 and/or WO2013072288 A1. For this variant of the invention, various cell culturing liquid (media) known in the art of cell culturing can be used, including one or more of the following media DMEM, HBSS, DPBS, RPMI, Iscove's medium, X-VIVO™, each optionally supplemented e.g. with fetal calf serum, human serum or serum substitutes or other nutrients or cell stimuli like Cytokines. The media can be standard cell media like the above mentioned media or special media for e.g. primary human cell culture (e.g. for endothelia cells, hepatocytes or keratinocytes) or stem cells (e.g. dendritic cell maturation, hematopoietic expansion, keratonocytes, mesenchymal stem cells or T cell expansion). The media may have supplements or reagents well known in the art, e.g. albumins and transport proteins, amino acids and vitamins, antibiotics, attachments factors, growth factors and cytokines, hormones or solubilising agents. Various media are commercially available e. g. from LifeTechnologies or Sigma-Aldrich.

The temperature during the cultivation process can be controlled and adjusted as appropriate for the cell types which have been electroporated. Furthermore, the cells may be supplied with gases such as $O_2$, $N_2$ and $CO_2$ as appropriate and known to a person skilled in the art. If the cell cultivation step is performed in a centrifuge chamber, the cells may be supplied with cell culturing liquids and gases during rotating the centrifuge chamber.

The cell type to be electroporated is not particular limited. With the method of the invention, especially eukaryotic cells, which may origin from any mammalian or human source, such as tumour, blood, tissue, bone marrow or cell lines can be processed. Suitable are for example, cell types selected from the group consisting of human cells, fibroblasts, embryonic stem cells, induced pluripotent cells, keratinocytes, melanocytes, mesenchymal stem cells, epithelial cells, T-cells, regulatory T-cells, B-cells, NK-cells, neuronal cells, dendritic cells, stem cells (adult, embryonic, hematopoietic), cells originating from epithelium, ectoderm, endoderm, endothelium, mesoderm, epithelial tissue, basal lamina, vasculature, connective tissue, fibrous tissues, Muscle tissue, visceral or smooth muscle, skeletal muscle, cardiac muscle, nervous tissue, brain, spinal cord, cranial nerves, spinal nerves or motor neurons.

The device and the method of the invention can be used in for continuous or semi-continuous electroporation process of cells, optionally followed by an cultivation (expansion) step of the electroporated cells. In order to reduce cell losses and/or contamination, a closed (as to the environment) system is proposed. Accordingly, a further object of the invention is a system for electroporation of cells comprising the disposable as disclosed, a first storage container containing a cell suspension; a second storage container containing a fluid comprising at least one compound to be electroporated into the cells; a third storage container for electroporated cells; a pump and/or a vacuum source; and a tubing set providing fluid communication between the storage containers and the disposable, wherein the system is closed to the outside atmosphere. Preferable, the third storage container is configured as cultivation chamber. If necessary, further storage containers for depleted/enriched cells fractions, washing fluids, cultivation media or waste may be provided.

The term "closed to the outside atmosphere" refers to a system which is configured to exclude any fluidic or gaseous exchange into the system, for example by using closed containers like plastic bags as storage container provided with mechanical connectors to the tubing set (like Luer connectors) and if necessary, appropriate sterile filters. In view of the process, the term "closed to the outside atmosphere" refers to a system which is configured to maintain sterility during the whole process of electroporation.

While various details have been described in conjunction with the exemplary implementations outlined above, various alternatives, modifications, variations, improvements, and/or substantial equivalents, whether known or that are or may be presently unforeseen, may become apparent upon reviewing the foregoing disclosure. Furthermore, details related to the specific methods, dimensions, materials uses, shapes, fabrication techniques, etc. are intended to be illustrative only, and the invention is not limited to such embodiments. Descriptors such as top, bottom, left, right, back front, etc. are arbitrary, as it should be understood that the systems and methods may be performed in any orientation. Accordingly, the exemplary implementations set forth above, are intended to be illustrative, not limiting.

EXAMPLES

Mixing ratio defined by the resistance channels

To determine the mixing ratio using the microfluidic channels, a phosphate buffered solution to mimic the cell suspension and an ink solution to mimic the nucleic acid solution was used. An electroporation cartridge as shown in FIGS. 1-7 was filed with these solutions by connecting to a vacuum line and the thus mixed solution was again removed from the cartridge. For several filling steps, the mixed solution has been collected and the mixing ratio was determined according to standard values determined by mixing different proportions of buffer and ink.

To determine the mixing ratio of the samples and standards, the absorption of the ink was measured using an optical photometer. 15 to 20 ml phosphate buffered solution was filled in a bag connected to the input port 120 of the electroporation cartridge by a short tube. A second bag filled with about 3 to 4 ml ink solution was connected to the second input port 110 of the electroporation cartridge by another short tube. The fluid of each tube was control by a punch valve. A peristaltic pump was connected to the exit port 140 via another tube. The connection of the pump to the electroporation cartridge could also be controlled by another punch valve. A fourth tube was connected on exit port 160 was used to collect the mixture of the two solutions. The exit fluid was also controlled by a punch valve. About 1 ml was filled in the electroporation cartridge and the absorbance of each cleared mixture was measured.

Figure 8:
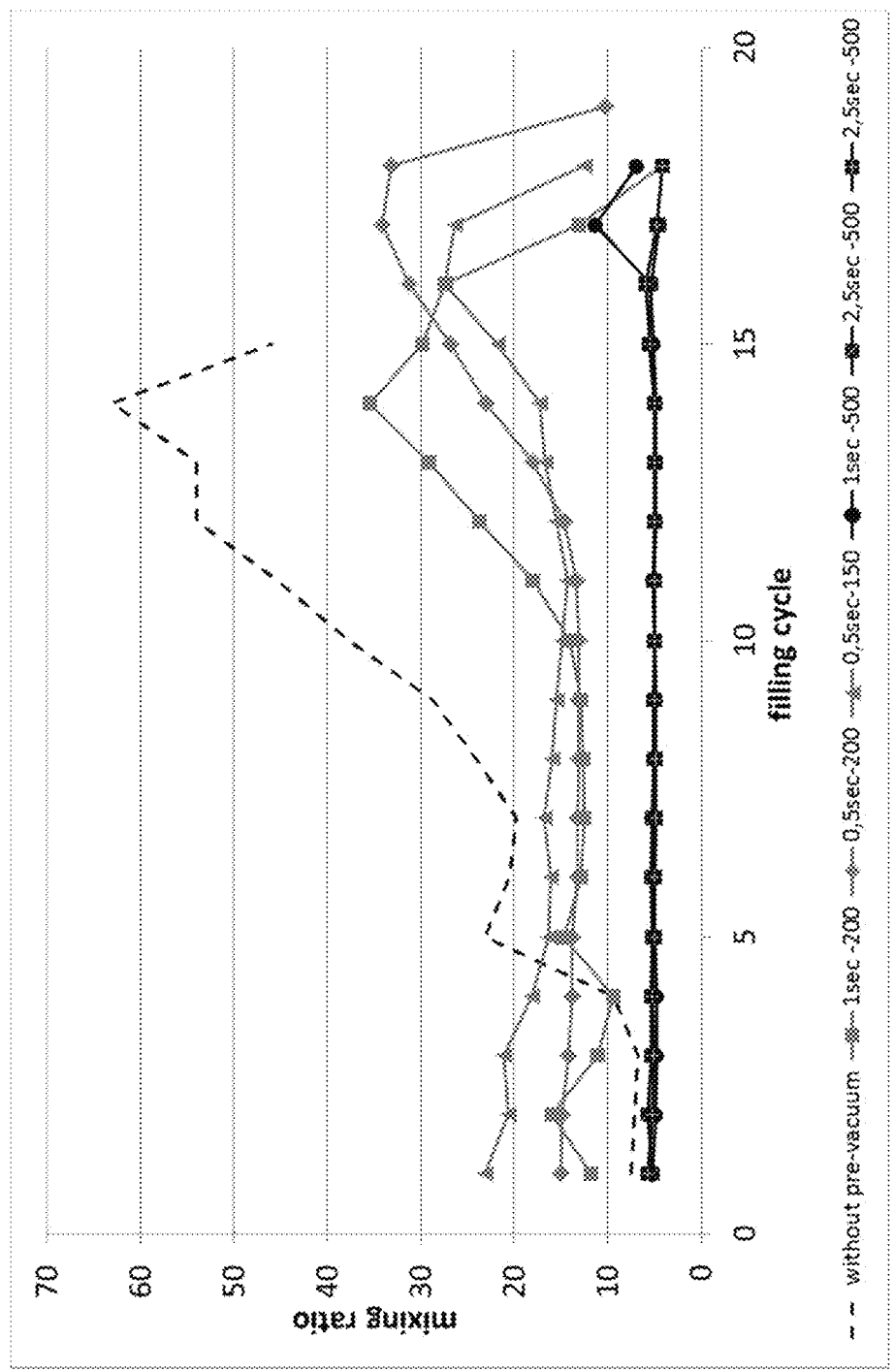
FIG. 8 shows the dependency of the mixing ratio and the vacuum within the electroporation cuvette
Figure 9:
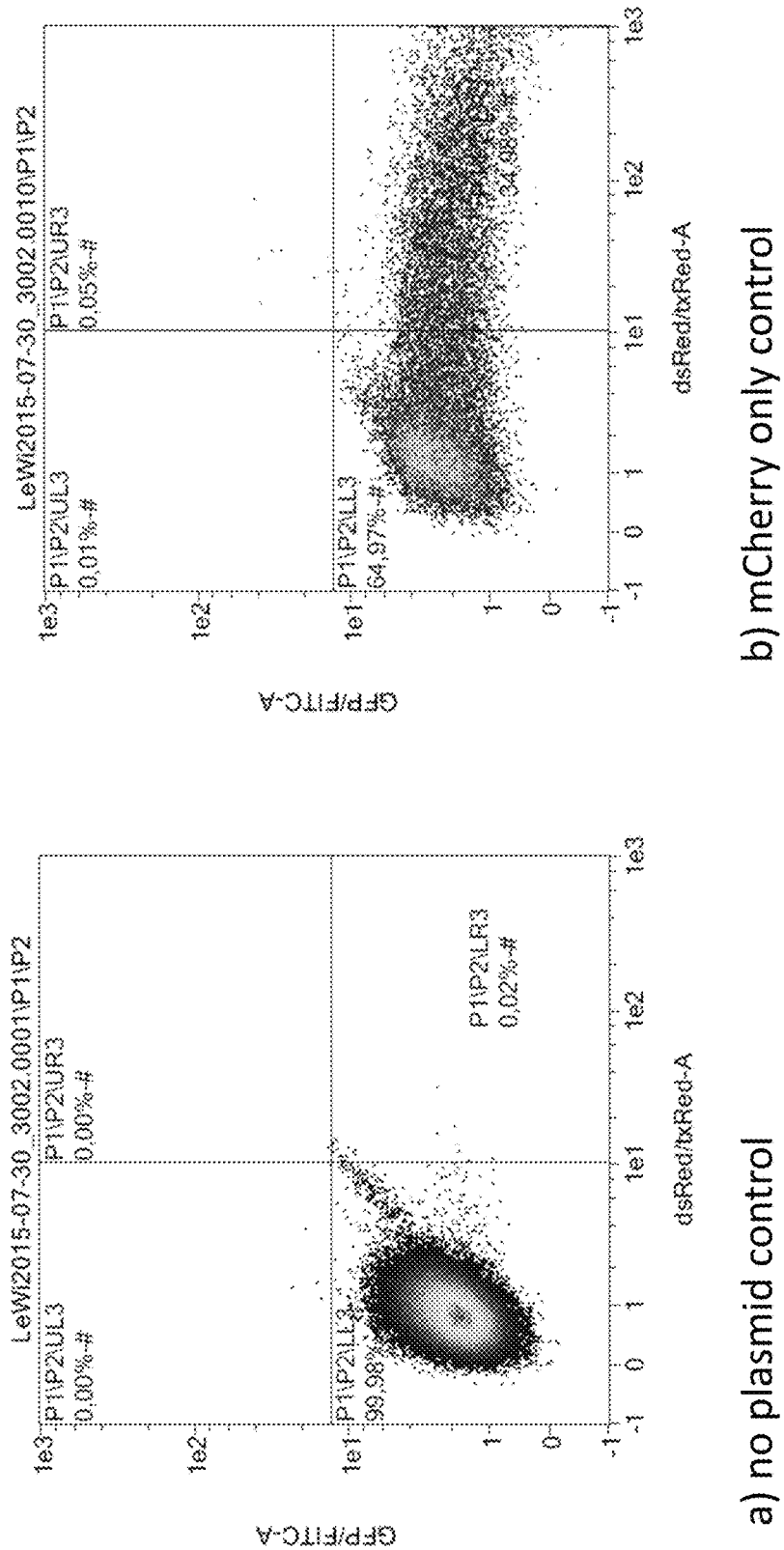
FIG. 9 shows the result of the electroporation of Jurkat cells with the transfection efficiency monitored by mCherry/eGFP expression It should be understood that the drawings are not necessarily to scale, and that like numbers may refer to like features.
Figure 9:
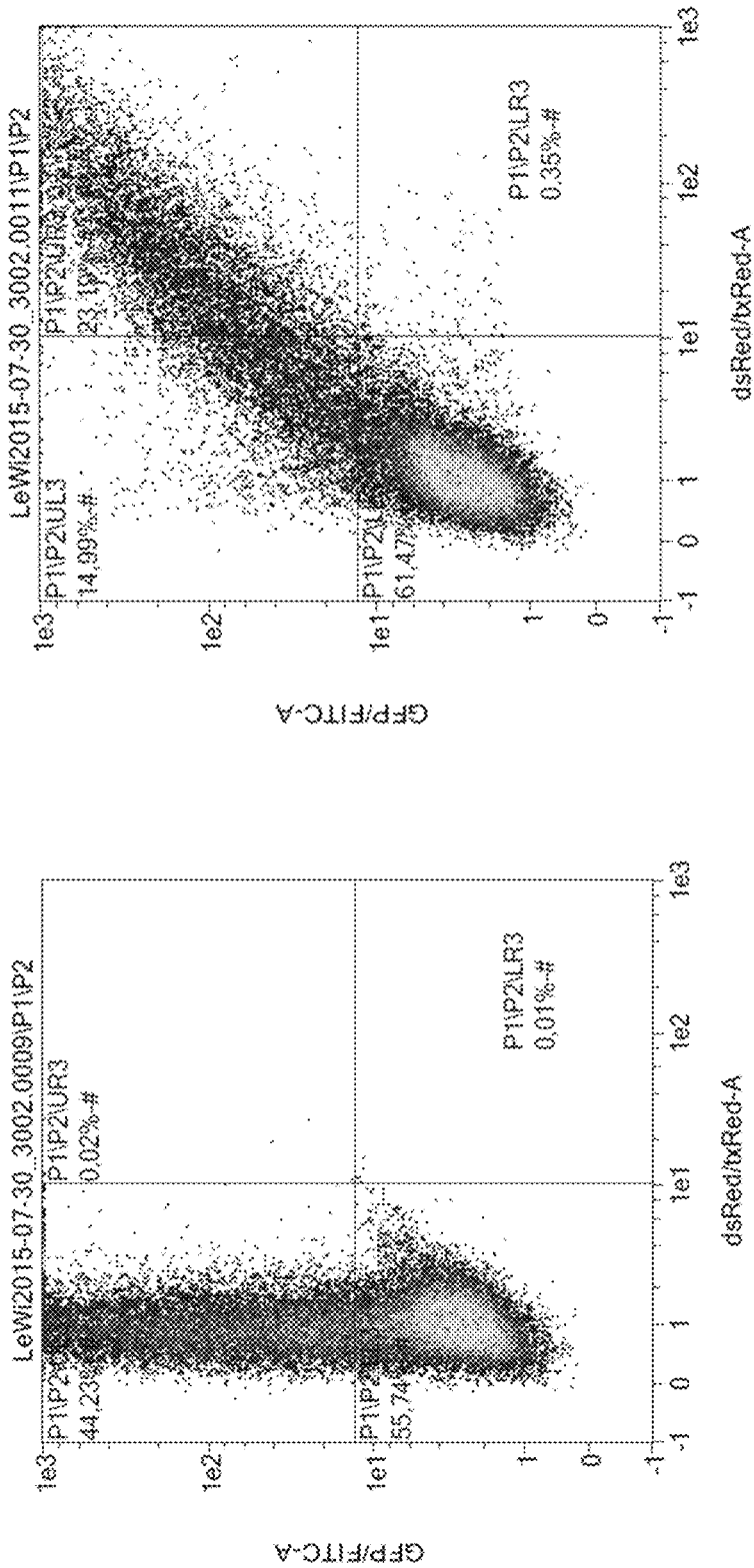
Figure 9:
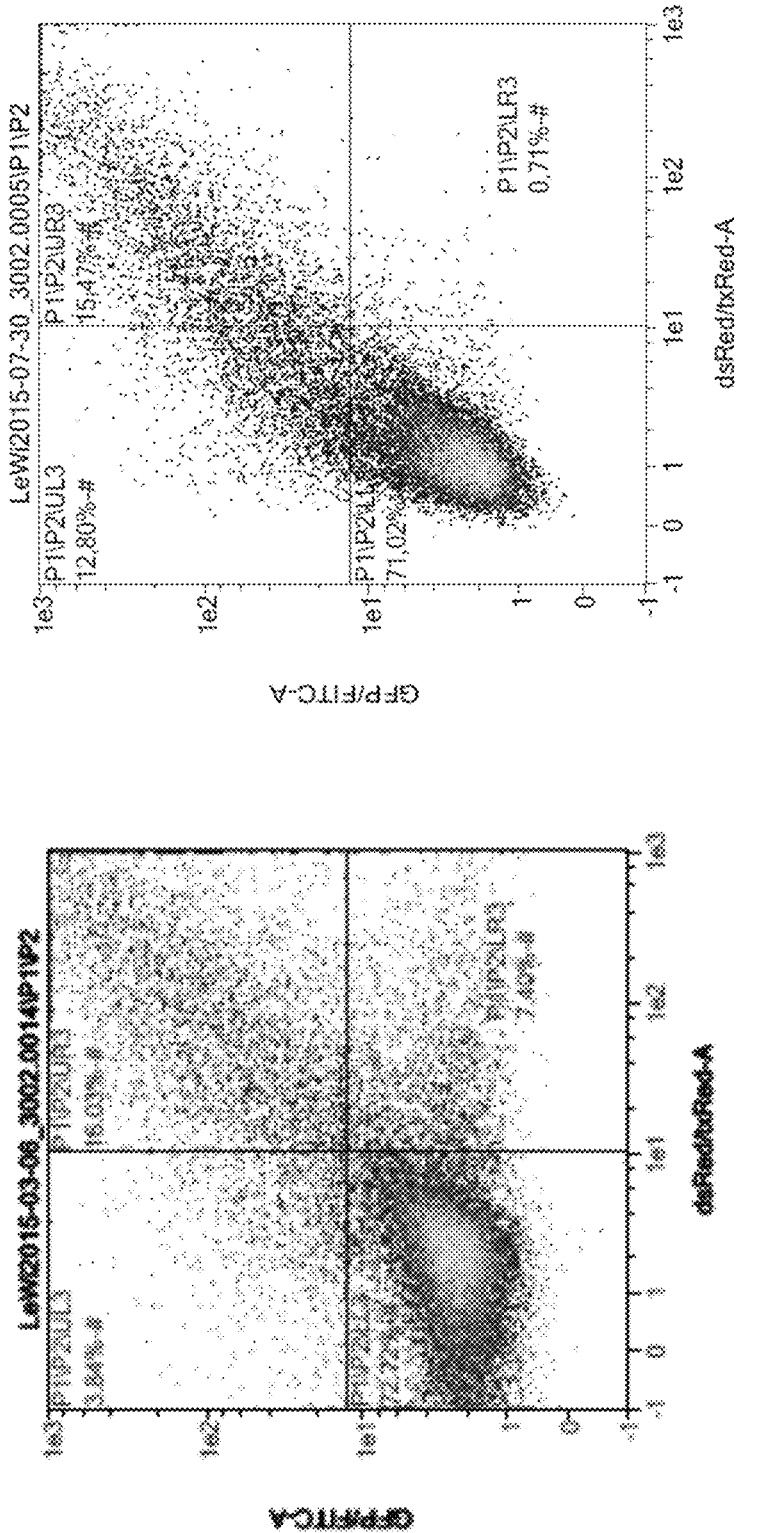

As shown in FIG. 8, the mixing ratio increases from about 1:7 to over 1:60 if two input valves and the exit valve 140 open simultaneously when the peristaltic pumps is started. As the fluid level in the bags and input tubes decrease, the hydrostatic pressure difference changes and thereby, the microfluidic mixing ratio is impaired (dashed line). When the peristaltic pump generates low vacuum in advance and then the valves open, we observed still an increase of the mixing ratio, but less dramatic. Further increasing the vacuum to less than −100 mbar gave a constant mixing ration of 1:5.1.

Electroporation

In order to prove the reliability of the device of the invention, a suspension of Jurkat cells was electroporated and after electroporation, the cells were analyzed by flow cytometer. The results are shown in FIG. 9a-g, with a) Control electroporation without plasmids, b) Control electroporation with only mCherry plasmid. c) Control electroporation with only eGFP plasmid. d) Control electroporation mCherry and eGFP plasmid manually mixed before electroporation. e) Electroporation cells premixed with mCherry plasmid and subsequently added eGFP plasmid without microfluidic mixing. f) Electroporation cells premixed with mCherry plasmid and eGFP plasmid added by microfluidic mixing. The following refers to FIG. 9:

Without any nucleic acids, no fluorescence was detected (a). Manually mixing the cells with a plasmid encoding the red fluorescent protein mCherry, about 35% of the cells express the red fluorescent protein as can be detected by the red fluorescence. Mixing the cells with a plasmid encoding the green fluorescent protein GFP, about 44% of the cells express the green fluorescent protein as can be detected by the green fluorescence. When both plasmids are manually mixed with the cell suspension, the electroporated cells fluorescence in red and green. The cells with the plasmid encoding the red fluorescent protein mCherry were manually mixed and applied to bag connected to the input port 120 of the electroporation cartridge by a short tube. A second bag filled with a solution containing a plasmid encoding the green fluorescent protein GFP was connected to the second input port 110 of the electroporation cartridge by another short tube. The fluid of each tube was controlled by a punch valve. A peristaltic pump was connected to the exit port 140 via another tube. The connection of the pump to the electroporation cartridge could also be controlled by another punch valve. A fourth tube connected on exit port 160 was used to collect the mixture of the two solutions. The exit fluid was also controlled by a punch valve. About 0.8 ml cell suspension was filled in the electroporation cartridge followed by about 0.2 ml nucleic acid solution. Then an electric pulse was applied. After the electroporation, the cell suspension was collected and the cells were analyzed by flow cytometry.

As can be seen in FIG. 9e, besides cells expression both fluorescent proteins, about 7% express only the red fluorescent protein. These cells were not well mixed with the green fluorescent protein encoding plasmid. Next, used cells were manually mixed with the plasmid encoding the red fluorescent protein mCherry and this mixture was applied in a bag connected to the input port 120 of the electroporation cartridge by a short tube. A second bag filled with a solution containing a plasmid encoding the green fluorescent protein GFP was connected to the second input port 110 of the electroporation cartridge by another short tube. The fluid of each tube was controlled by a punch valve. A peristaltic pump was connected to the exit port 140 via another tube. The connection of the pump to the electroporation cartridge could also be controlled by another punch valve. A fourth tube connected on exit port 160 was used to collect the mixture of the two solutions. The exit fluid was also controlled by a punch valve. About 1 ml was filled in the electroporation cartridge using the microfluidic mixing channels and the microfluidic mixing element 130. Then an electric pulse was applied. After the electroporation, the cell suspension was collected and the cells were analyzed by flow cytometry. FIG. 9f) shows that electroporated cells express both fluorescent proteins showing the homogenous mixing of the cells with the nucleic acid solution of the green fluorescent protein encoding plasmid.

While various details have been described in conjunction with the exemplary implementations outlined above, various alternatives, modifications, variations, improvements, and/or substantial equivalents, whether known or that are or may be presently unforeseen, may become apparent upon reviewing the foregoing disclosure. Accordingly, the exemplary implementations set forth above, are intended to be illustrative, not limiting.

What is claimed is:

1. A disposable cartridge for electroporation of cells, comprising
    a fluid compartment in an interior of the disposable cartridge;
    a first fluid inlet port for providing a first fluid comprising a cell suspension to the fluid compartment, and a second fluid port for delivering a second fluid comprising at least one compound to be electroporated into the cells to the fluid compartment;
    a first electrode and a second electrode disposed in the fluid compartment, with a voltage applied between the first and second electrodes, wherein the first and second electrodes are spaced such that an electric field of more than 2 kV/cm is formed between the first and the second electrodes;
    at least one exit port which delivers the fluid from the fluid compartment, wherein the first inlet port and the second fluid ports have a fluid communication to a mixing channel which has a fluid communication to the fluid compartment; and a third ground electrode disposed in the first fluid inlet port and a fourth ground electrode disposed in the at least one exit port, and the third and fourth ground electrodes are not between the first and the second electrodes and configured to remove charge from cell suspension, and wherein a voltage pulse is applied between the first and the second electrodes, and the third and fourth electrodes are configured to apply ground potential to the cell suspension in the first fluid inlet port and the at least one exit port.

2. The disposable cartridge of claim 1, wherein the fluid compartment has a non-rectangular parallelogram shape with one corner higher than the others, and wherein the at least one exit port and the first fluid inlet port are disposed at the highest and lowest corners of the parallelogram fluid compartment, respectively and wherein the mixing channel has a serpentine shape and/or comprises agitator elements or a mixing chamber.

3. The disposable cartridge of claim 1, wherein the first fluid inlet port and the second fluid port are each provided with a channel each having a different microfluidic resistance.

4. The disposable cartridge of claim 3, wherein the first fluid inlet port and the second fluid port are each provided with a channel each having a different microfluidic resistance, so as to maintain a mixing ratio of 1:5 to 1:10 of the first fluid to the second fluid.

5. The disposable cartridge according to claim 1, wherein the first fluid inlet port and the second fluid port are in fluid communication with at least one pump delivering fluids from the first fluid port and the second fluid into the fluid compartment.

6. The disposable cartridge according to claim 1, wherein the at least one exit port is in fluid communication to at least one vacuum source thereby sucking fluids from the first fluid port and the second fluid into the fluid compartment.

7. The disposable cartridge according to claim 1, wherein the mixing channel and the at least one exit port are located at opposite sides of the fluid compartment to enable bubble-free filling of the fluid compartment with fluid.

8. The disposable cartridge according to claim 1, wherein the first electrode and the second electrode comprise titanium covered with a layer of gold.

9. A process for electroporation of cells in the disposable cartridge of claim 1, wherein a cell suspension is provided to a first fluid inlet port as first fluid and a fluid comprising at least one compound to be electroporated into the cells is provided to the second fluid port as second fluid; the first and second fluids are provided to the fluid compartment in predefined mixing ratio by applying a pressure difference between the first and second fluid ports and at least one exit port; applying a pulsed electric field between the first and second electrodes thereby electroporating the cells with at least one compound; and removing the fluids from the fluid compartment; and applying a ground potential to the cell suspension by the third and the fourth electrodes disposed at the first fluid inlet port and the at least one exit port.

10. The process according to claim 9, wherein the first and second fluids are provided to the fluid compartment to a predefined filling level; and wherein the filling level of the fluid compartment is determined by measuring the capacitance between the first and second electrode.

11. The process according to claim 9 wherein after removing the fluids from the fluid compartment, the electroporated cells are detected and depleted from the fluids.

12. The process according to claim 9, wherein after removing the fluids from the fluid compartment, the electroporated cells are cultivated.

13. A system for electroporation of cells comprising the disposable cartridge according to claim 1, a first storage container containing a cell suspension; a second storage container containing a fluid comprising at least one compound to be electroporated into the cells; a third storage container for electroporated cells; a pump and/or a vacuum source; and a tubing set providing fluid communication between the first, second and third storage containers and the disposable cartridge, wherein the system is closed to outside atmosphere.

14. The system according claim 13, wherein the third storage container is configured as a cultivation chamber.

15. The disposable cartridge of claim 1, wherein the voltage pulse is at least one of exponentially decaying, square wave, and combinations thereof.

16. A method for creating pores in a cell membrane, comprising:
providing the disposable cartridge of claim 1,
filling the disposable cartridge of claim 1 with a suspension of cells;
mixing the suspension; and
electroporating the cells by applying a pulse of at least 2 kV/cm to create pores in the cell membranes.

17. The disposable cartridge of claim 1, wherein the first and second electrodes fit conformally within the fluid compartment, wherein both the fluid compartment and the first and second electrodes have acute and obtuse angles.

18. The disposable cartridge of claim 1, wherein both the first and second electrodes and the fluid compartments have a shape of a trapezoid or parallelogram, with the trapezoid of the first and second electrodes fitting within the trapezoid of the fluid compartment.

* * * * *